United States Patent [19]
Seth et al.

[11] Patent Number: 6,012,327
[45] Date of Patent: Jan. 11, 2000

[54] GAS SENSOR AND METHOD FOR MANUFACTURING THE SAME

[75] Inventors: Michael Seth, Linden; Maximilian Fleischer, Hoehenkirchen; Hans Meixner, Haar, all of Germany

[73] Assignee: Siemens Aktiengesellschaft, Munich, Germany

[21] Appl. No.: 08/854,482

[22] Filed: May 12, 1997

[30] Foreign Application Priority Data

May 10, 1996 [DE] Germany .......................... 196 18 935

[51] Int. Cl.[7] .................. G01N 7/00; G01N 27/04
[52] U.S. Cl. ............................................. 73/31.06; 422/90
[58] Field of Search ...................... 73/31.06, 23.2, 73/23.21; 422/98, 90, 94

[56] References Cited

U.S. PATENT DOCUMENTS

| | | |
|---|---|---|
| 4,347,732 | 9/1982 | Leary . |
| 4,601,914 | 7/1986 | Barnes et al. .............................. 438/49 |
| 5,635,628 | 6/1997 | Fleischer et al. ...................... 73/31.06 |
| 5,767,388 | 6/1998 | Fleischer et al. ...................... 73/31.06 |

FOREIGN PATENT DOCUMENTS

| | | |
|---|---|---|
| 0 464 243 B1 | 1/1992 | European Pat. Off. . |
| 0 527 258 B1 | 2/1993 | European Pat. Off. . |
| 0743515A1 | 5/1996 | Germany ........................ G01N 27/12 |

*Primary Examiner*—Hezron Williams
*Assistant Examiner*—Jay Politzer
*Attorney, Agent, or Firm*—Hill & Simpson

[57] ABSTRACT

A gas sensor and method for manufacturing a gas sensor is provided. In order to increase the selectivity and the sensitivity to a gas to be measured, a gas-sensitive gallium oxide layer of a gas sensor is coated with a filter layer that comprises silicon dioxide. In an alternative embodiment, the gallium oxide layer can be coated with a gas-sensitive metal oxide layer made of titanium oxide, aluminum vanadate, tungsten oxide or tantalum oxide.

2 Claims, 17 Drawing Sheets

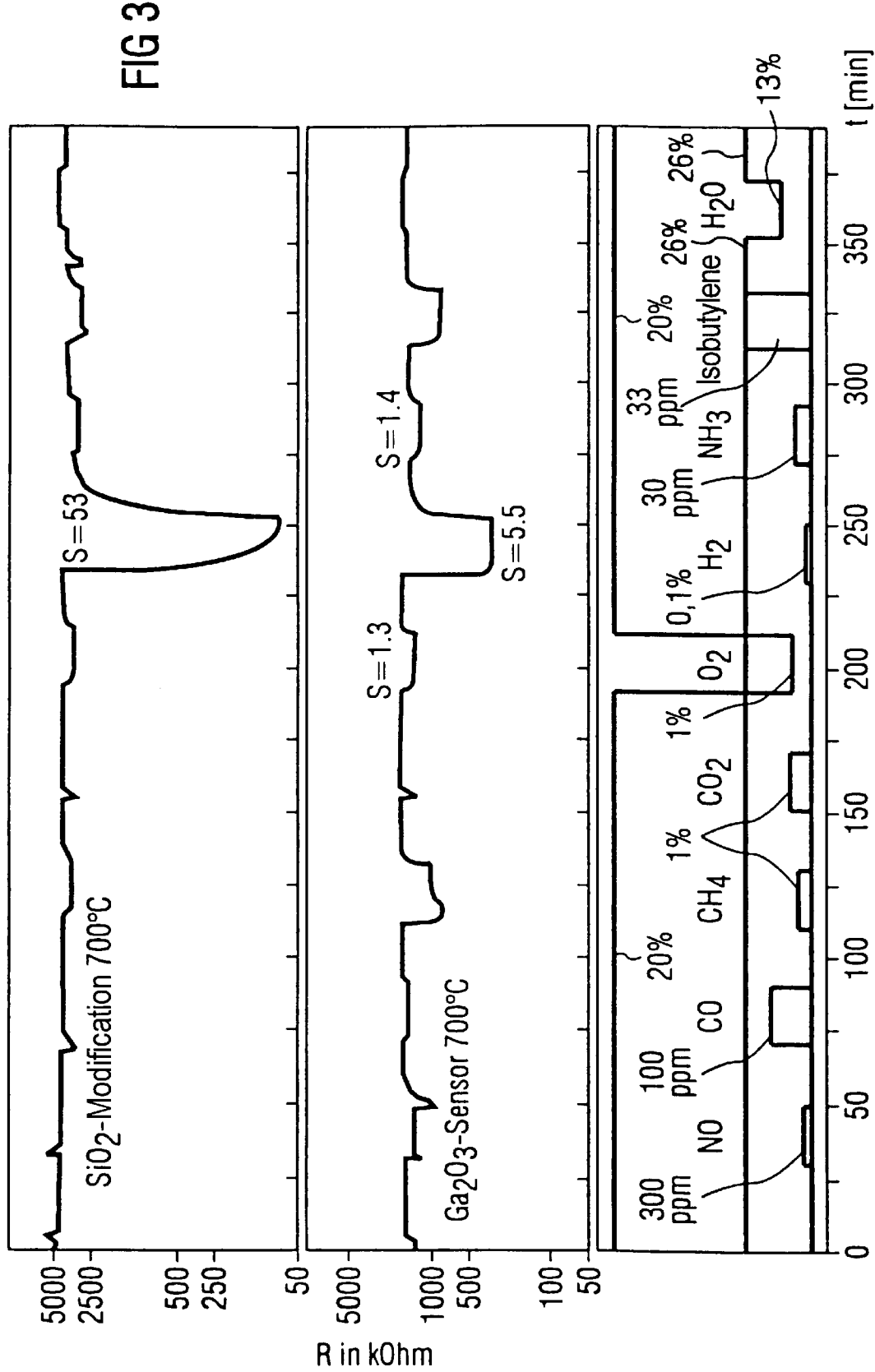

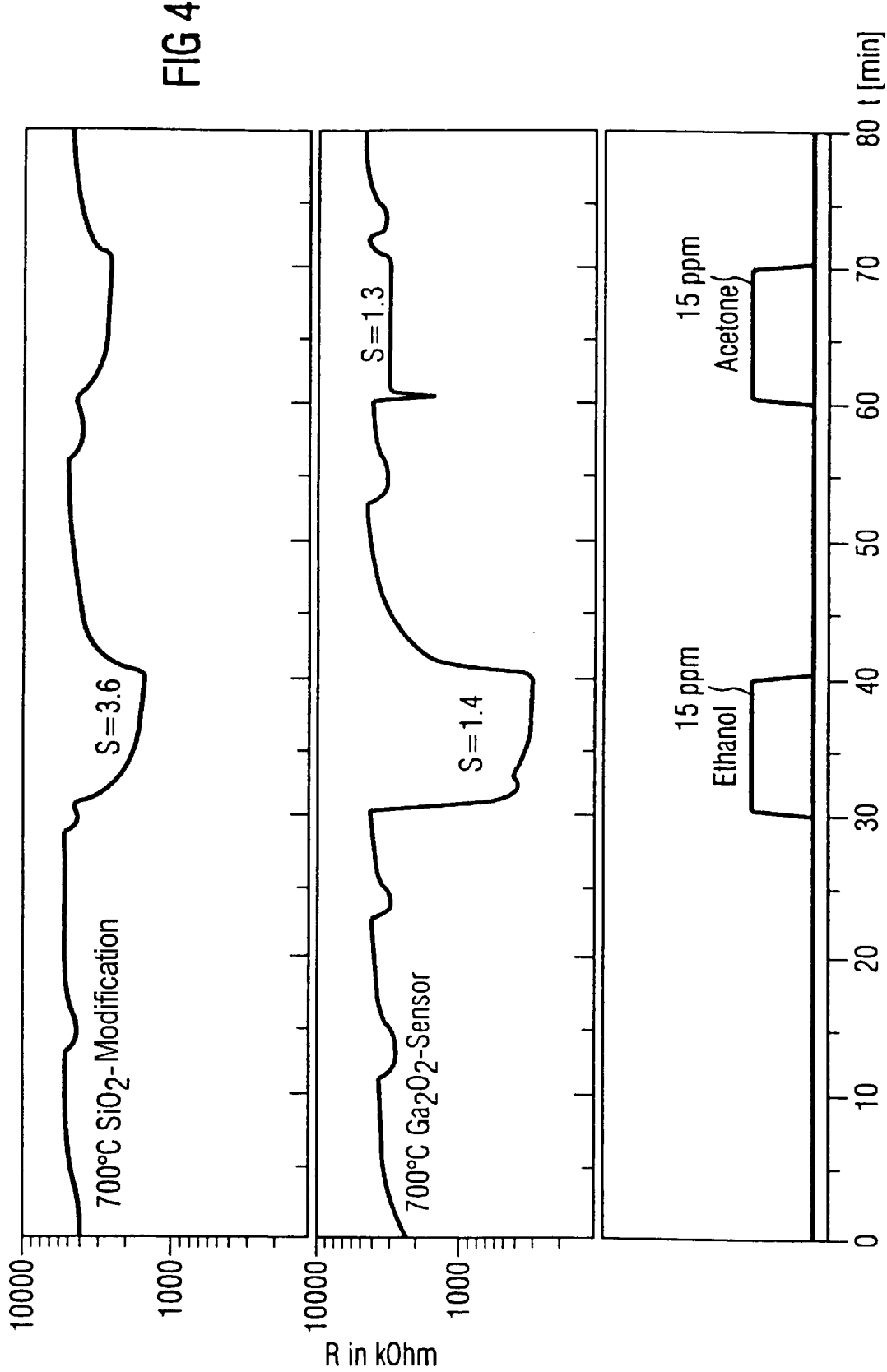

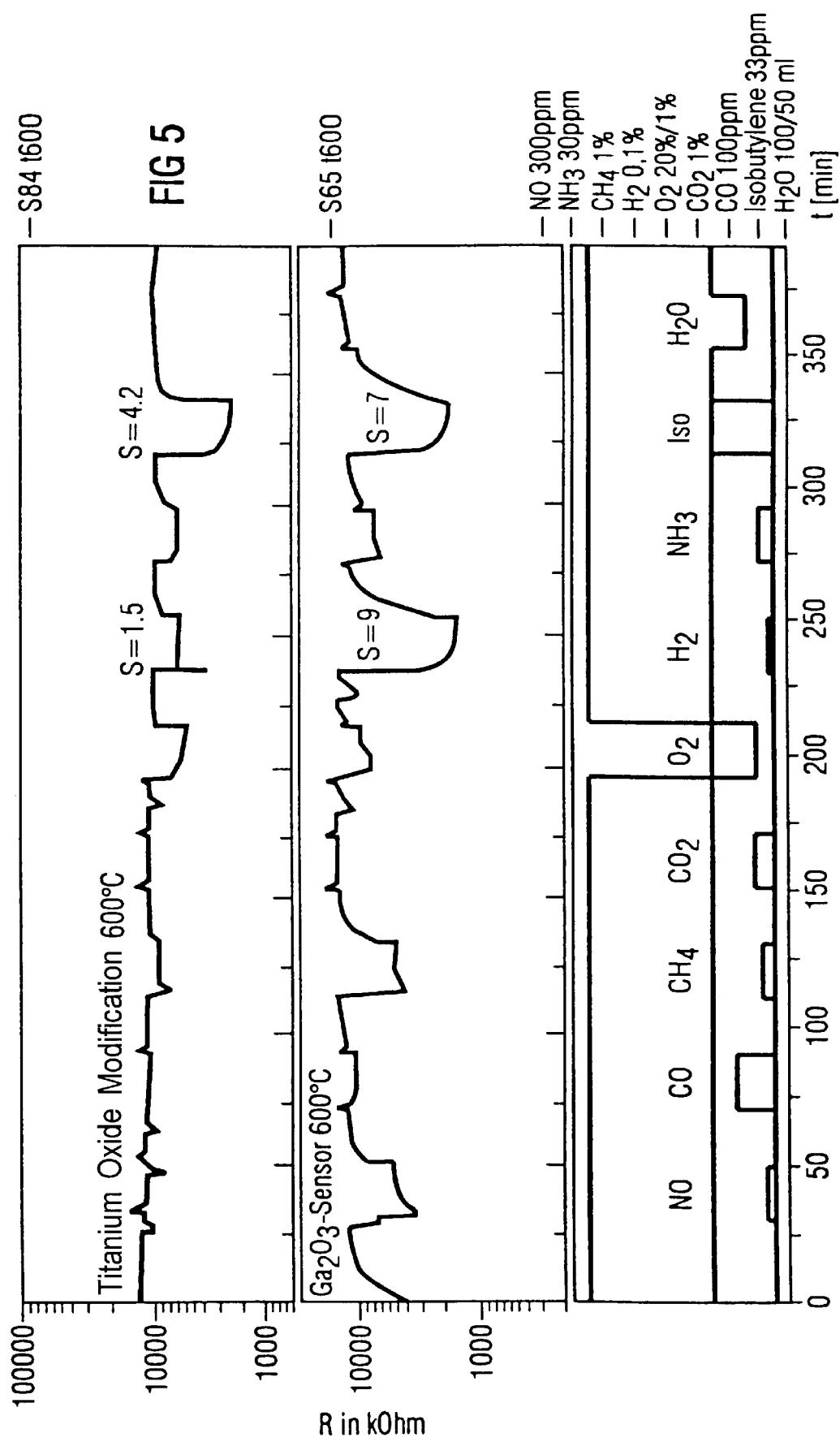

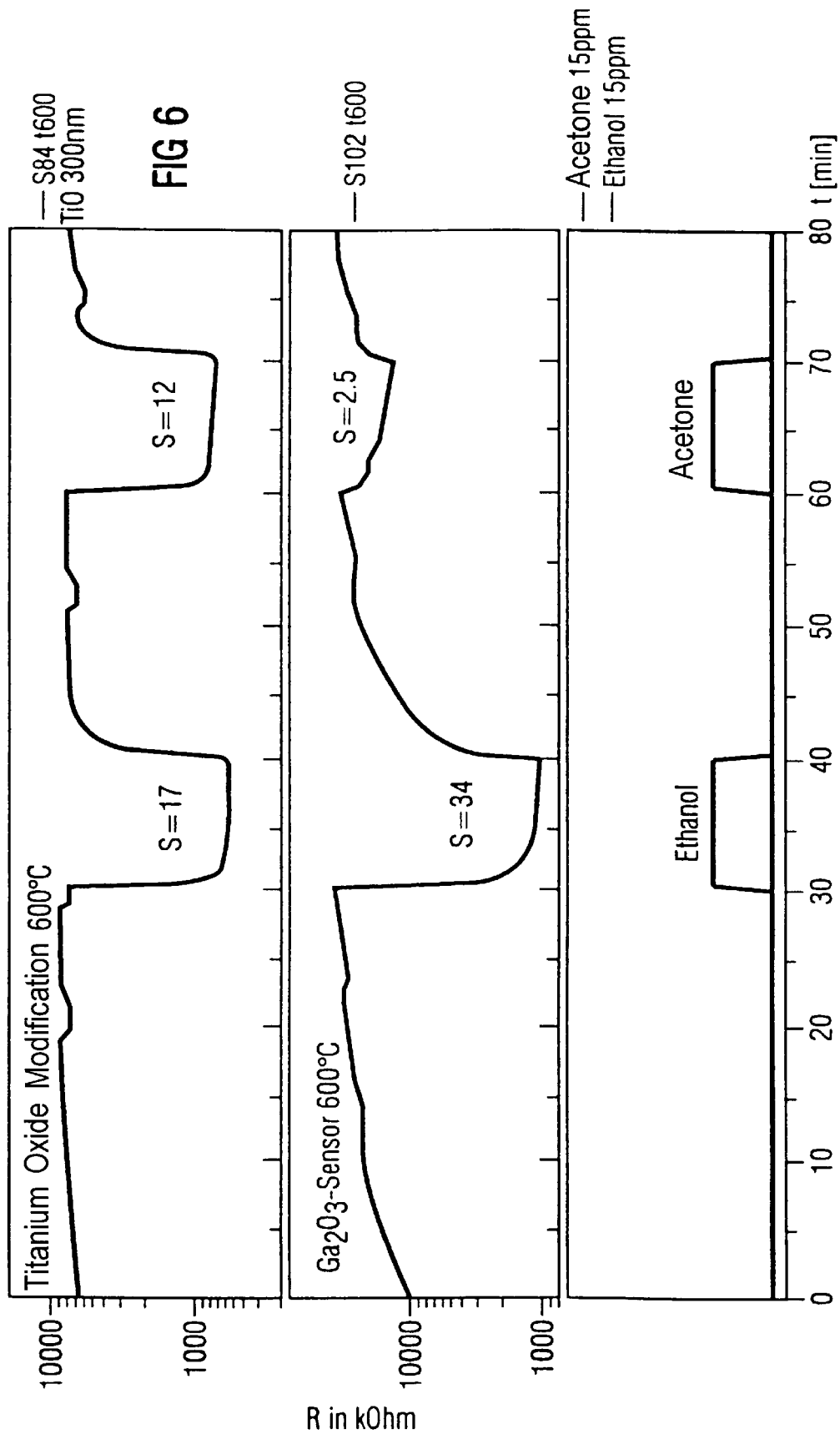

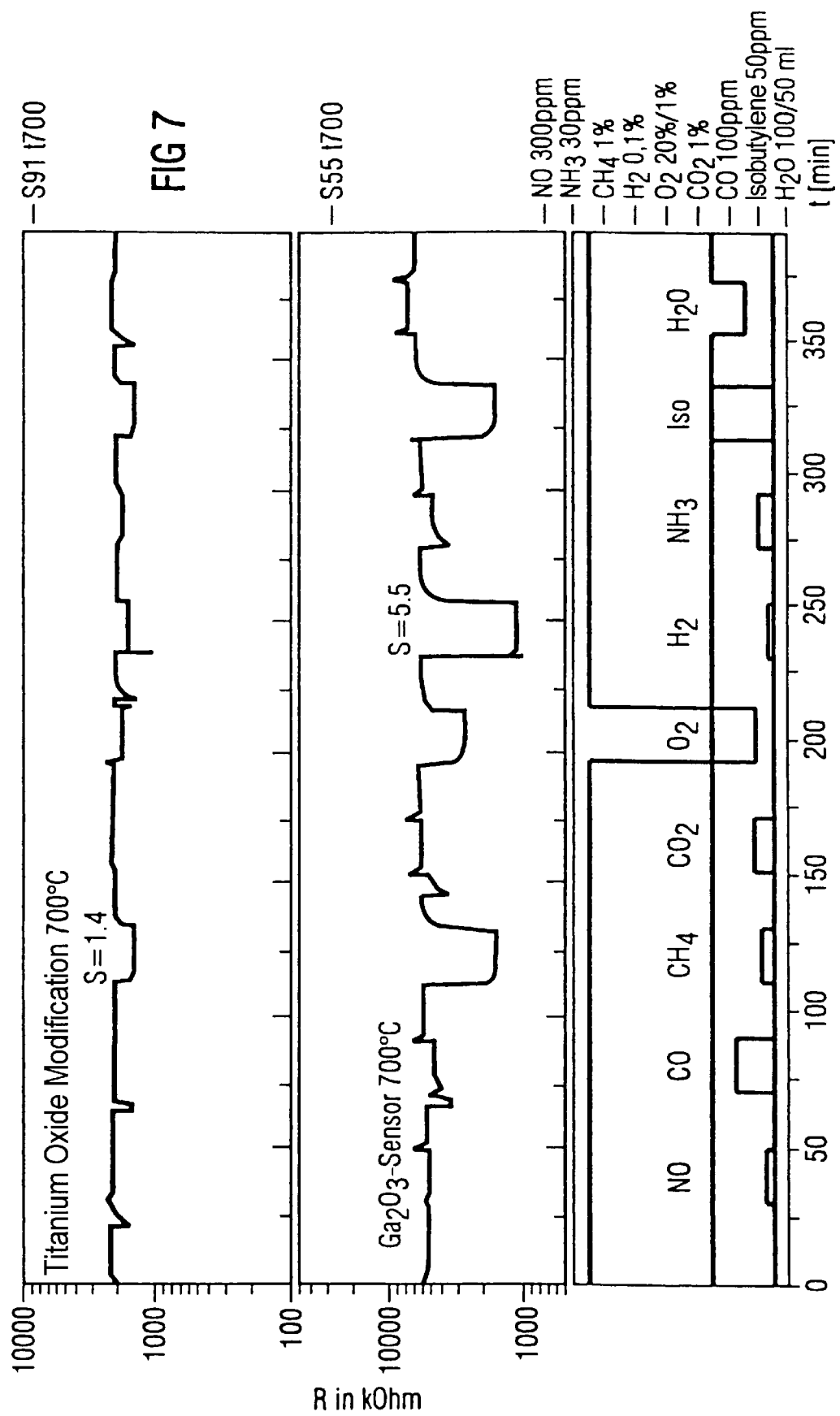

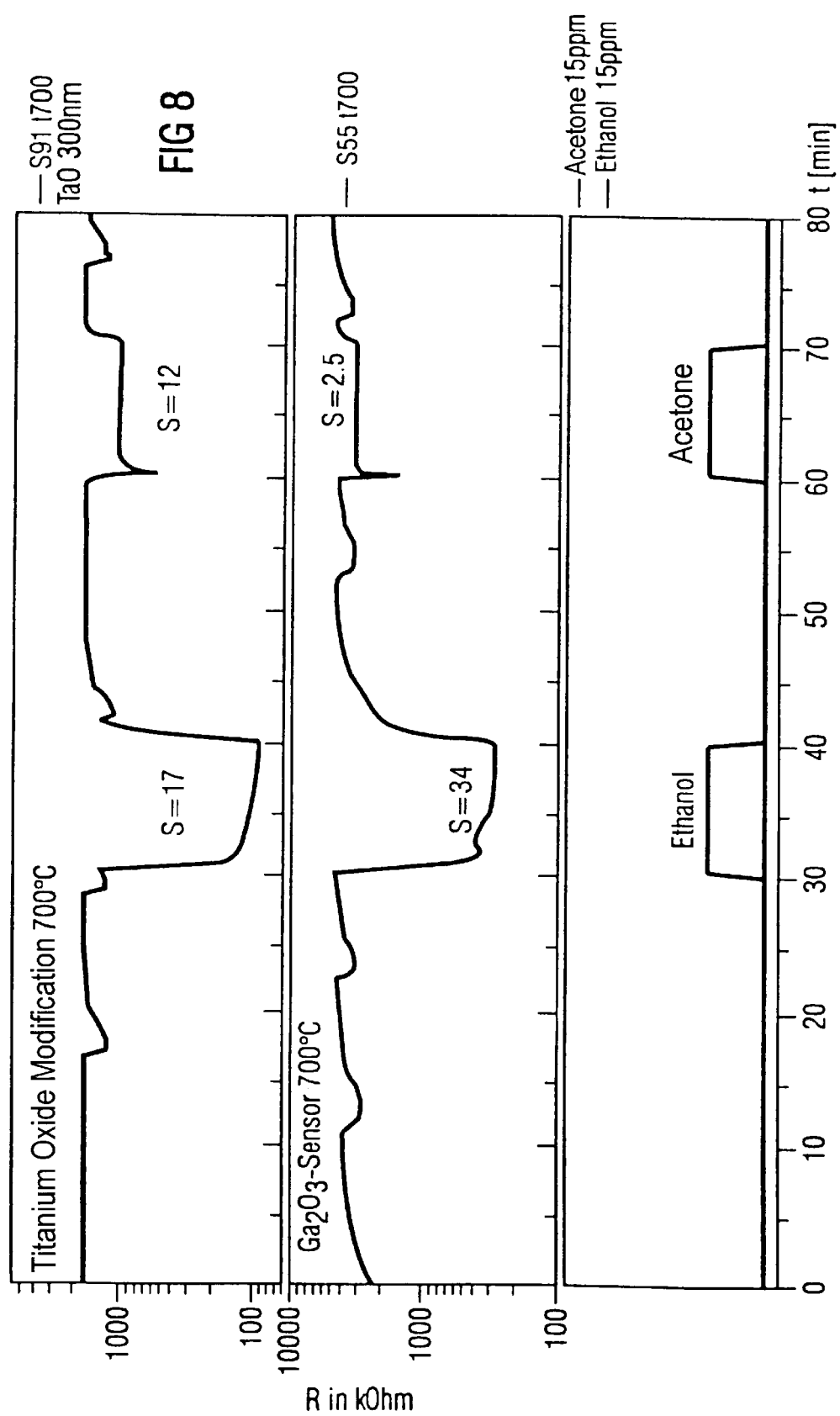

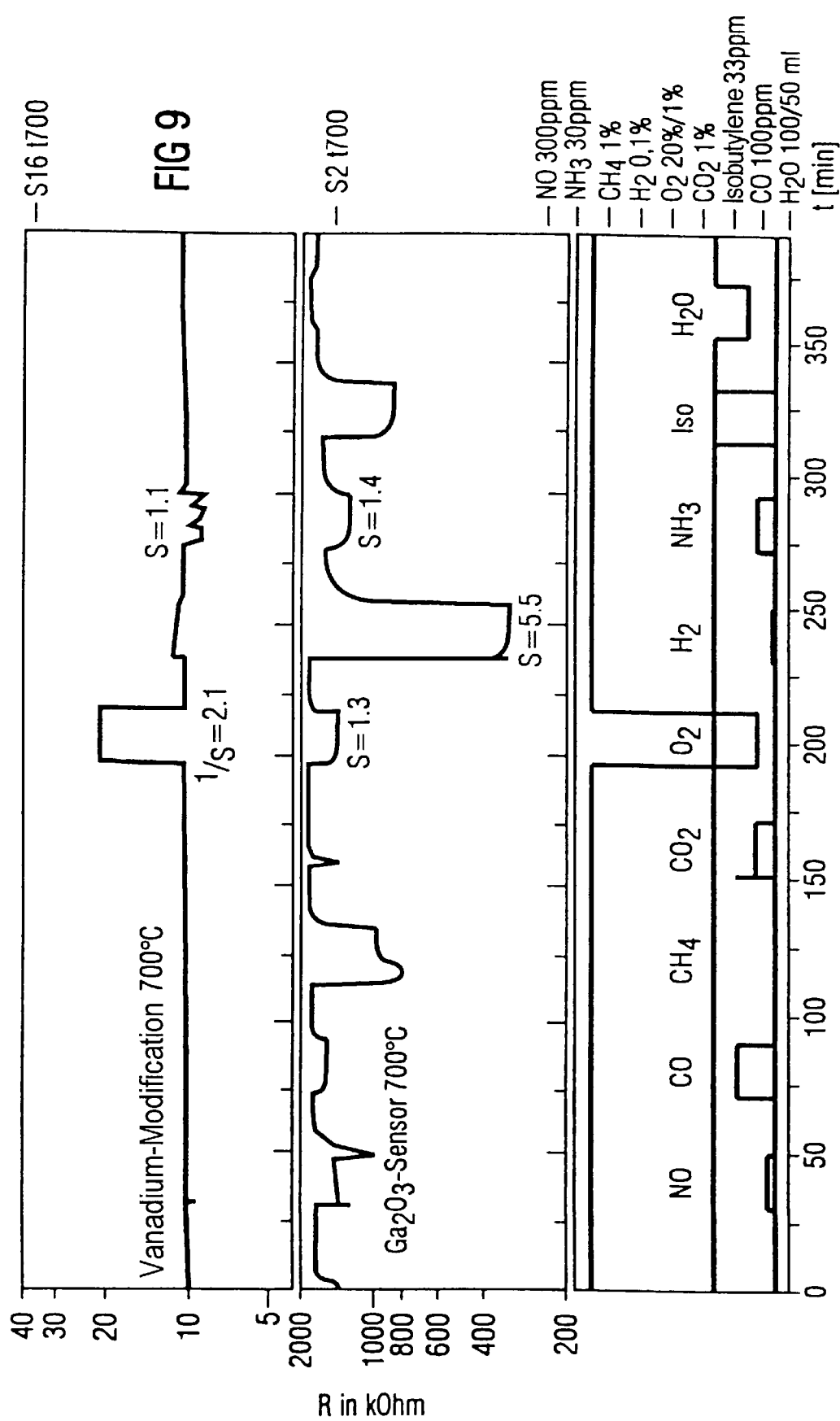

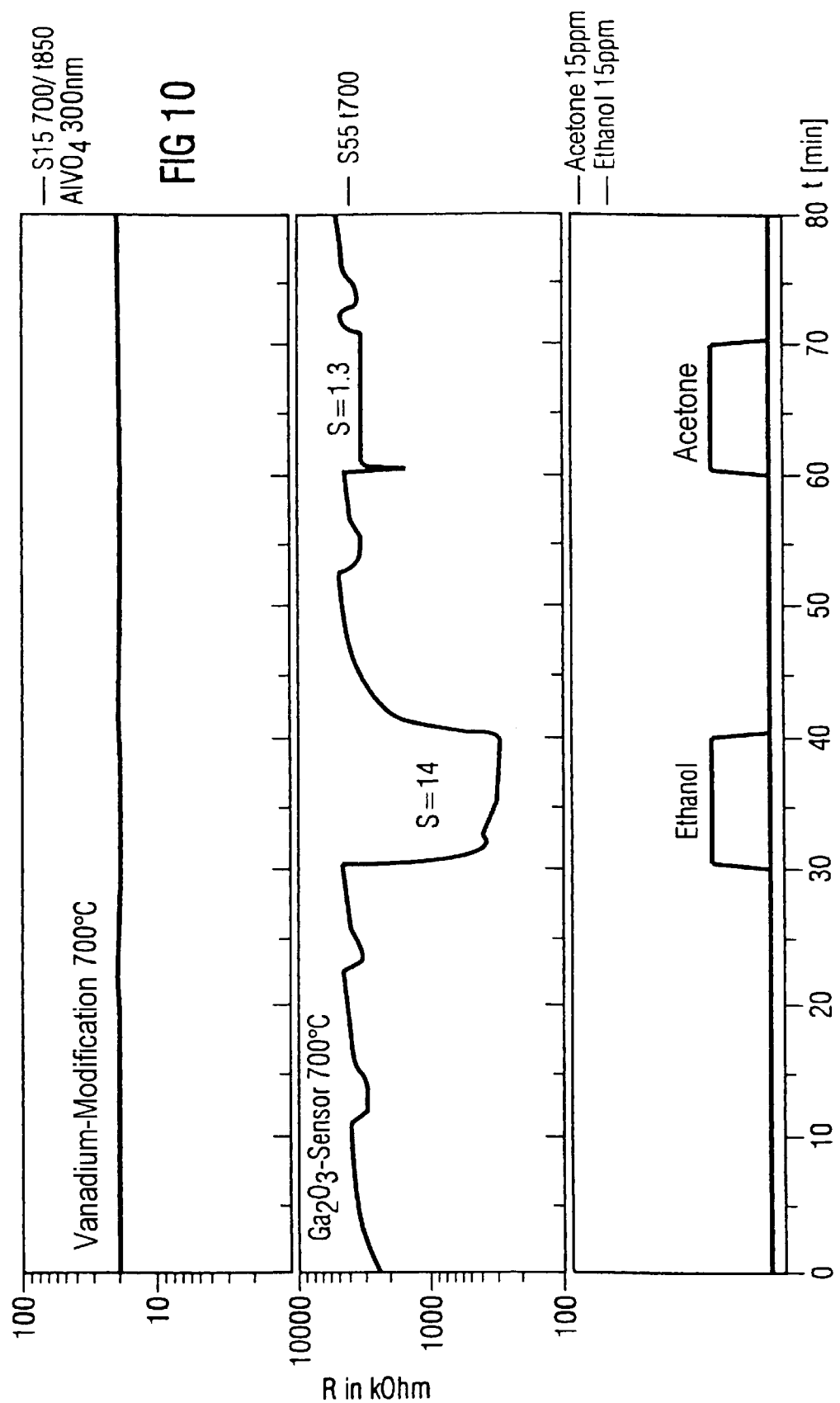

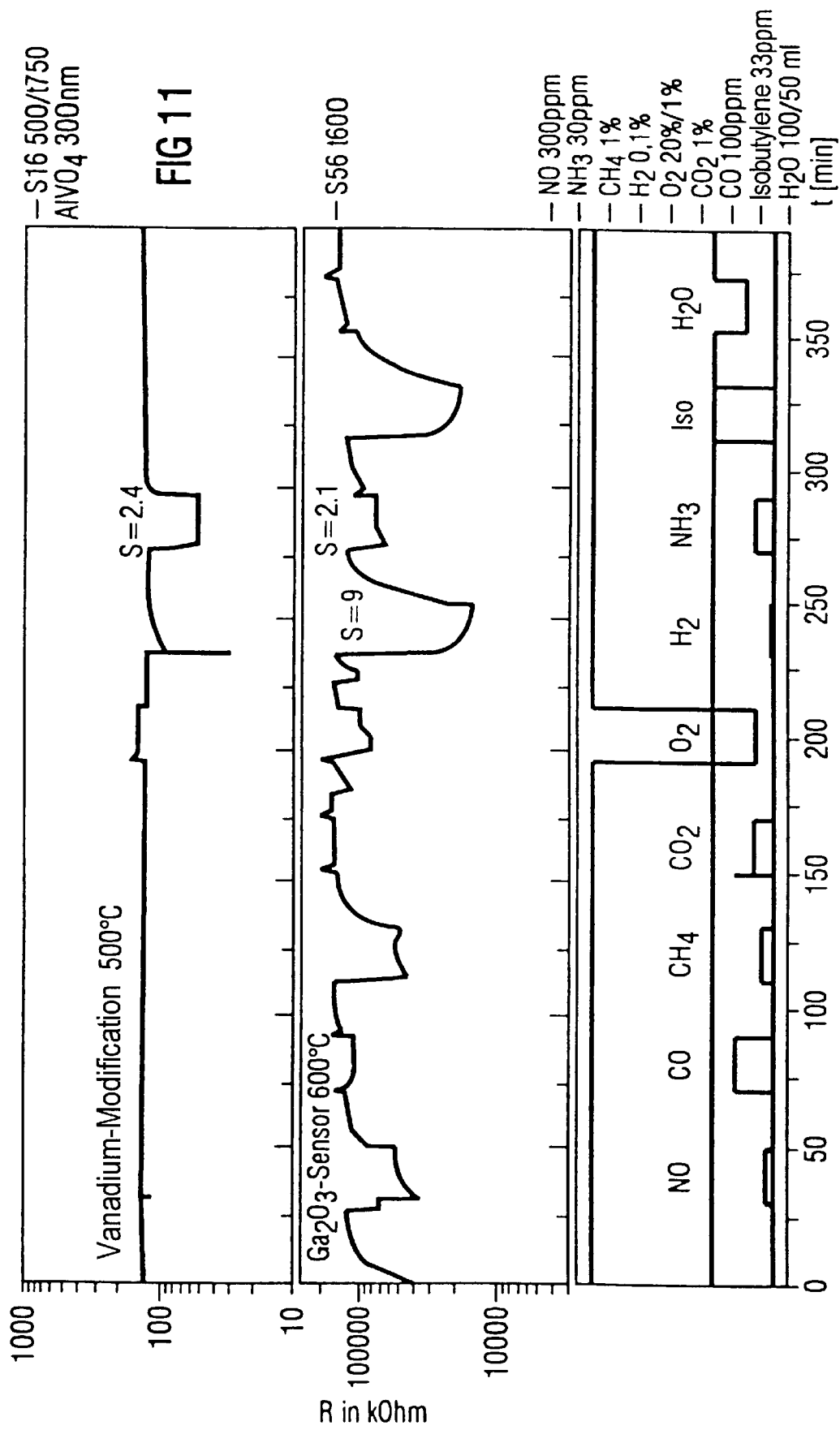

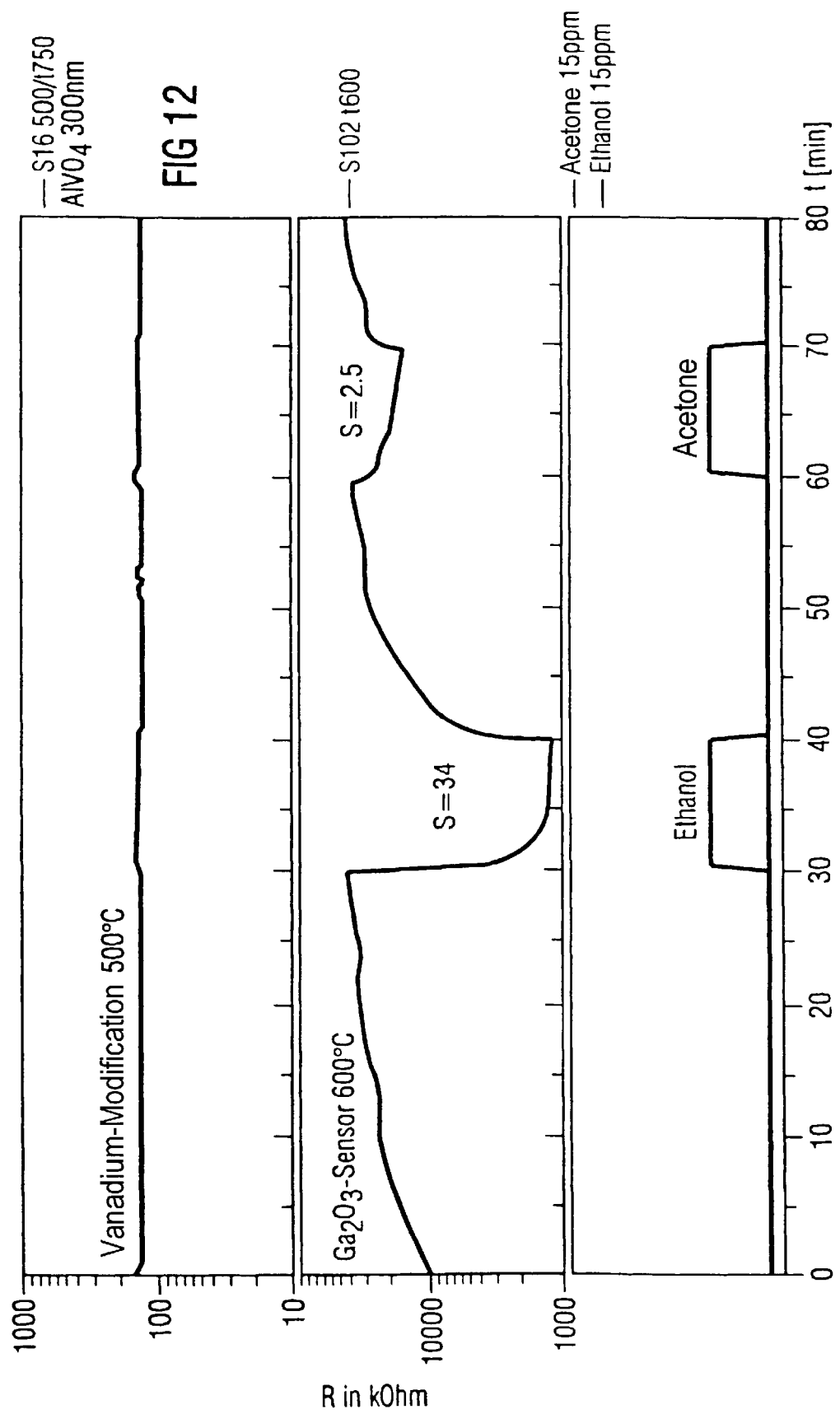

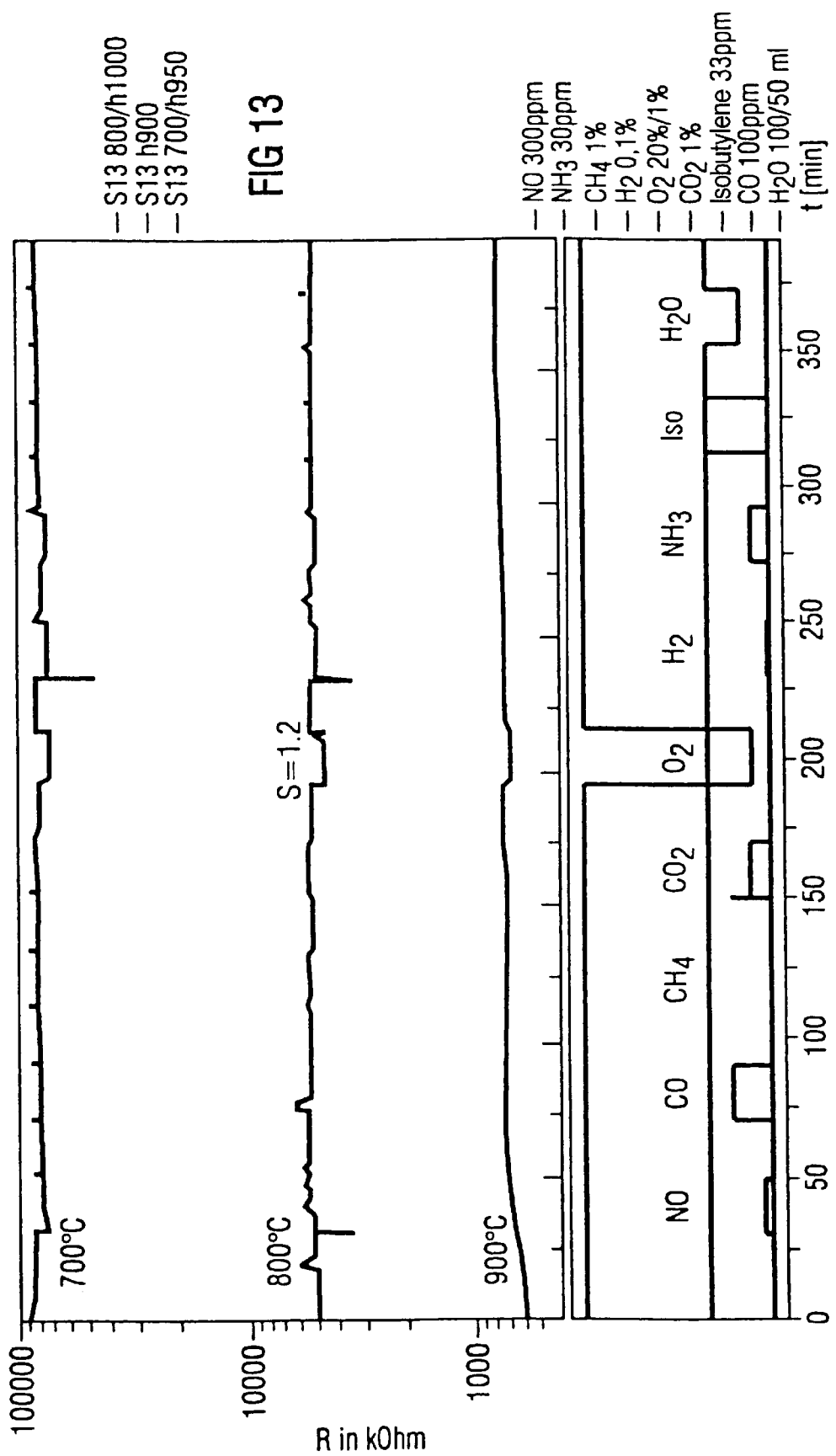

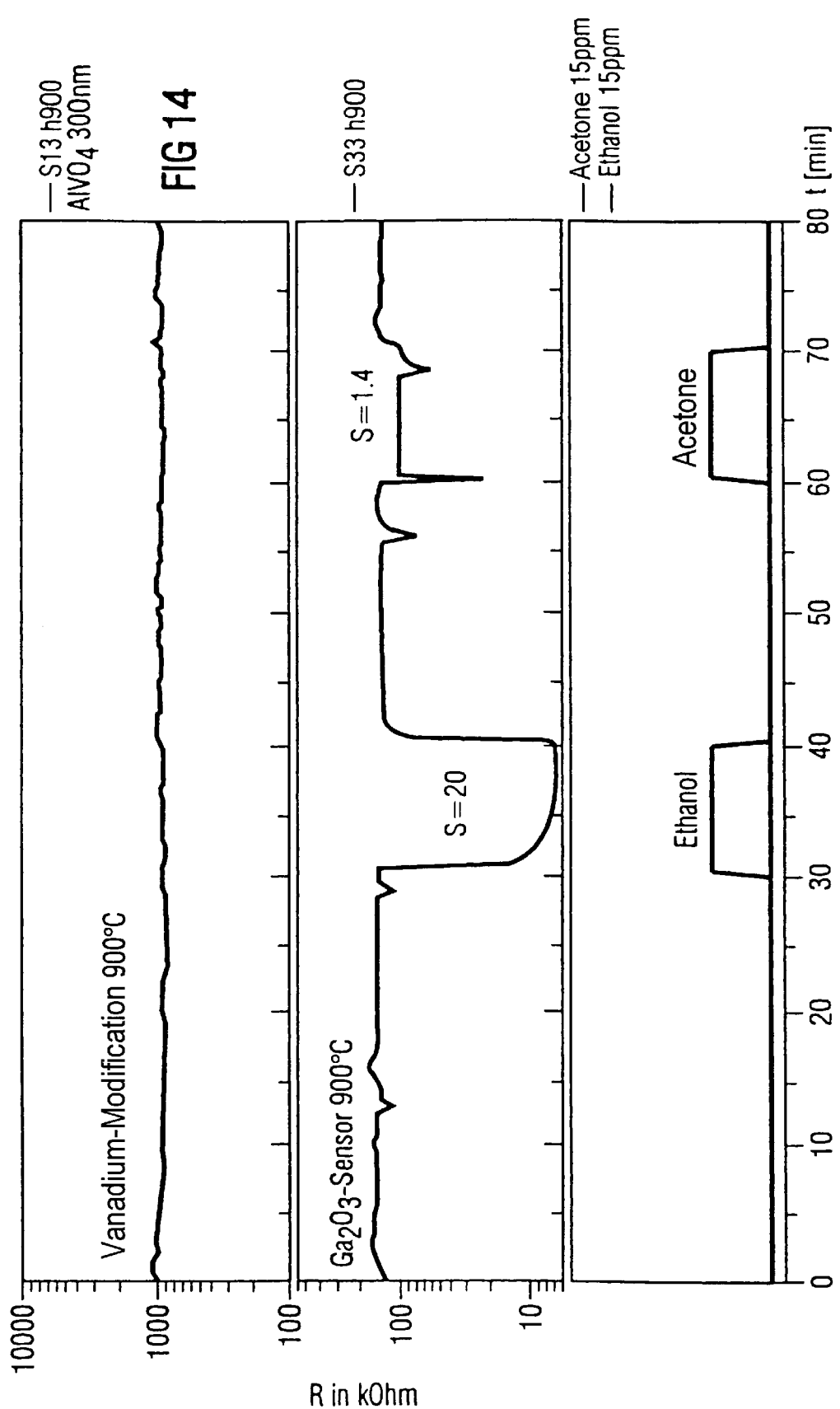

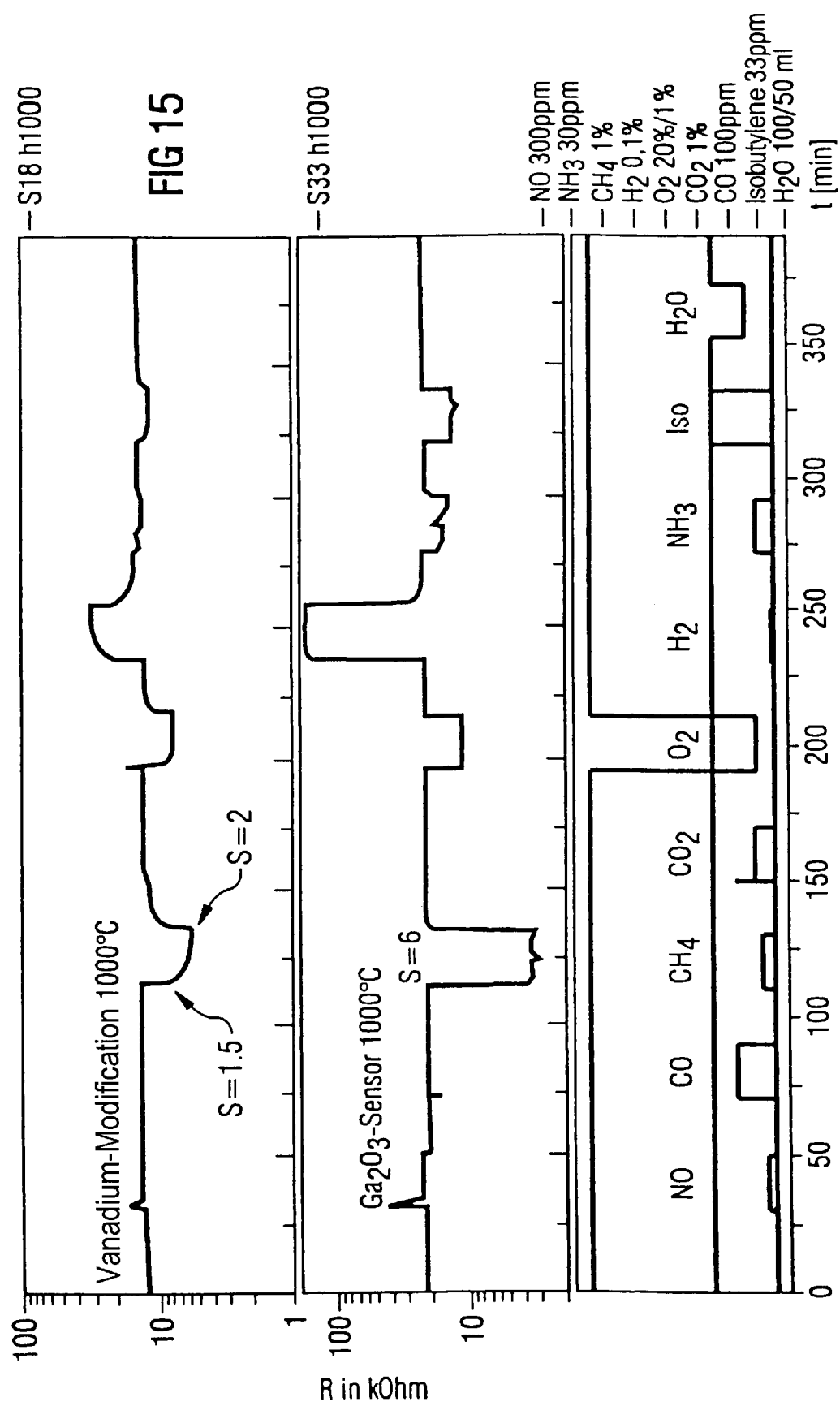

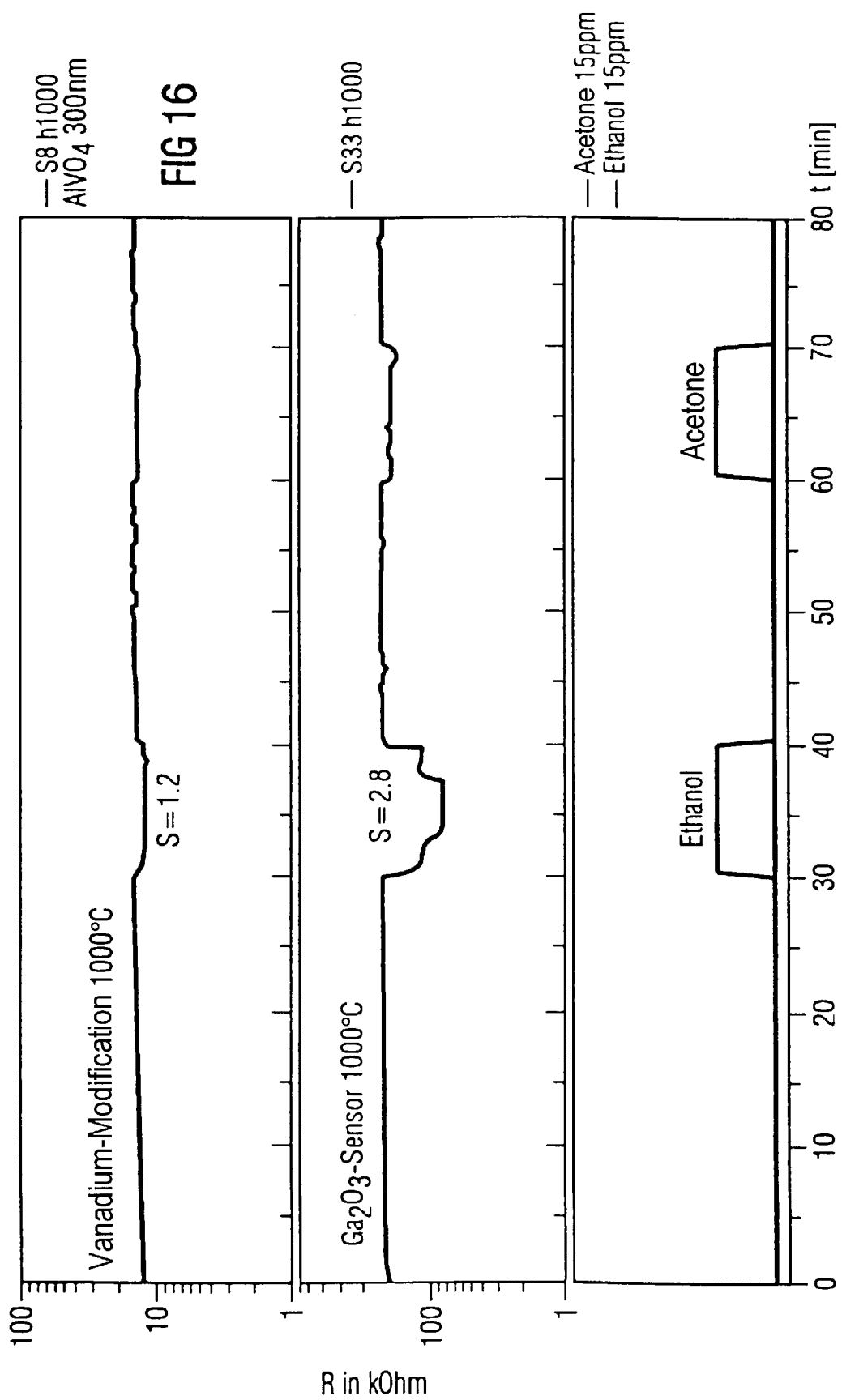

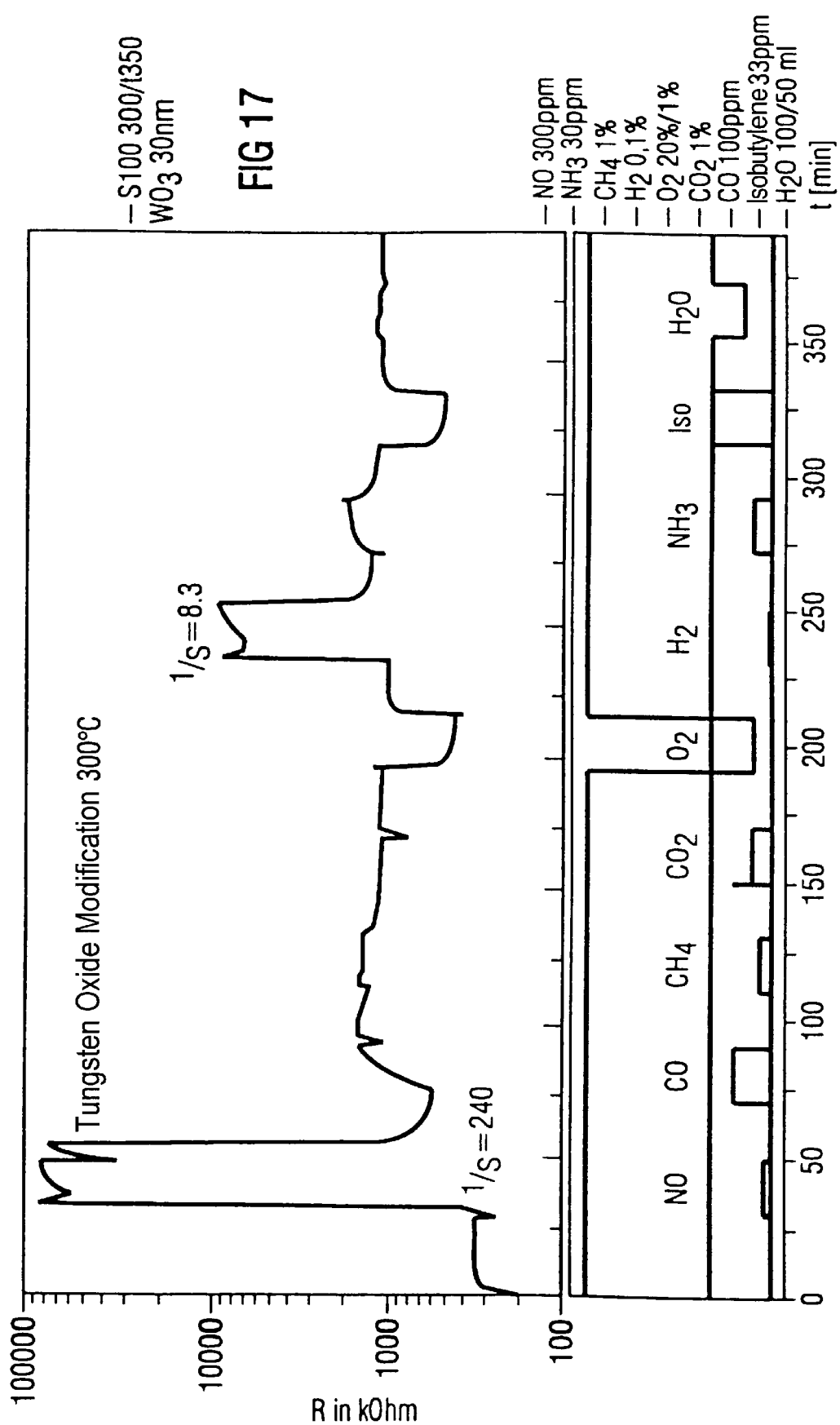

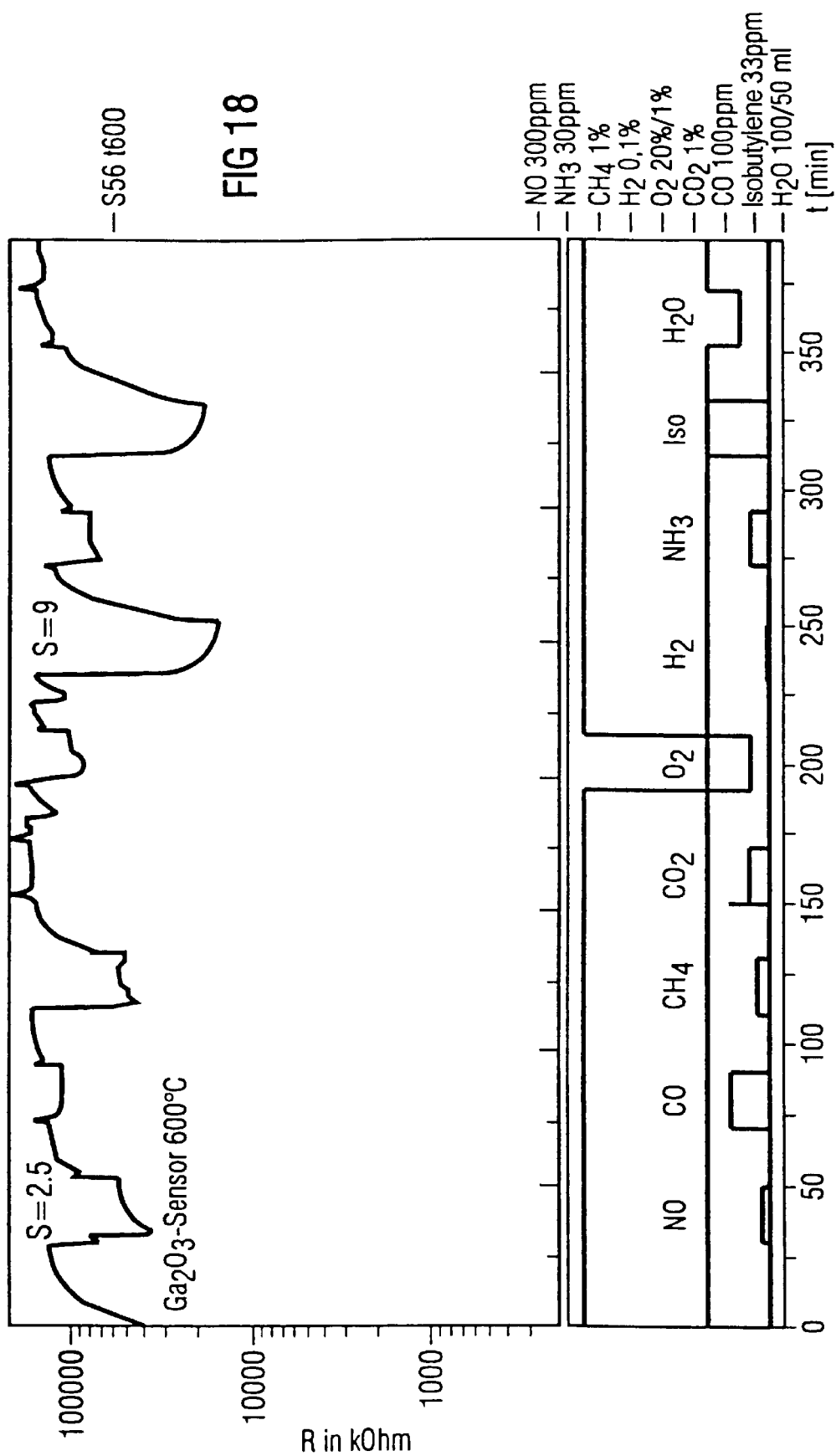

GAS SENSOR AND METHOD FOR MANUFACTURING THE SAME

The present invention is related to gas sensors, and more specifically, to gas sensors made from a metal oxide. Still more specifically, the present invention relates to metal oxide gas sensors for detecting a gas in a gas mixture.

Previously, it was only possible to influence the gas-sensitive characteristics of the metal oxide by changing the operating temperature, and thereby increasing the sensitivity to particular gases and reducing it to other gases. On this subject, we refer to the two references EP 0 527 258 B1 and EP 0 464 243 B1. In the last-named reference, an oxygen sensor with a semiconducting gallium oxide is specified. If the operating temperature of the gas sensor is higher than 850° C., the oxygen content of the material interacts with the oxygen content of the surrounding atmosphere, so that the specific electrical conductivity of the material is a measure of the currently prevailing oxygen partial pressure. If a gas sensor is to be created for reducing gases, then, according to EP 0 527 258 B1, the operating temperature for the $Ga_2O_3$ thin layer is about 600° C.

A gas sensor for detecting particular combustible and toxic gases is known from the prior art U.S. Pat. No. 4,347,732. The gas sensor has a gas-sensitive layer that contains gallium oxide doped with zinc oxide. This layer is covered with a filtering layer made of a zeolite, e.g. zeolite 3 A. The gas sensor is operated at a temperature of 200° C. The gas sensor is not suited for temperatures between 600 and 1000° C., since a vaporization of the zeolite layer occurs in this temperature region.

SUMMARY OF THE INVENTION

An object of the present invention is to provide a gas sensor whose selectivity and sensitivity is increased in relation to the gas to be measured.

In an embodiment, the present invention provides a gas sensor which comprises a gas-sensitive layer disposed on a substrate. The gas-sensitive layer comprises gallium oxide. A filter layer is disposed on top of the gas-sensitive layer. In an embodiment, the filter layer comprises silicon dioxide.

In an embodiment, the thickness of the filter layer ranges from about 300 nm to about 500 nm.

In an embodiment, the gas-sensitive layer has a thickness of about 2 $\mu$m.

In an embodiment, the sensor of the present invention has an operating temperature ranging from about 600° C. to about 700° C.

The present invention also provides a method for manufacturing a gas sensor which comprises the steps of depositing a gas-sensitive layer comprising gallium oxide on a substrate and thereafter depositing a filter layer comprising silicon dioxide on the gas-sensitive layer. The deposition of the silicon dioxide may be accomplished by a process selected from the group consisting of cathode sputtering, CVD, electron beam vaporization, molecular beam vaporization and a wet-chemical process. In an embodiment, the gallium oxide layer is tempered prior to the deposition of the filter layer on the gallium oxide layer. Further, in an embodiment, the sensor undergoes a second tempering process after the deposition of the filter layer.

In an embodiment, a gas sensor of the present invention comprises a first metal oxide layer comprising gallium oxide and a second layer disposed above the first metal oxide layer which comprises a gas-sensitive metal oxide. The gas-sensitive metal oxide of the second layer is selected from the group consisting of $TiO_2$, $V_2O_5$, $WO_3$, TaO, MgO, $ZrO_2$ and BeO.

In an embodiment, the second layer has a thickness ranging from about 30 nm to about 300 nm.

In an embodiment, the sensor has an operating temperature ranging from 300° C. to about 1000° C.

In an embodiment, a method of manufacturing a gas sensor in accordance with the present invention includes the step of depositing a gallium oxide layer on a substrate followed by the step of depositing a second layer comprising a gas-sensitive material selected from the group consisting of $TiO_2$, $WO_3$, TaO, $AlVO_4$, MgO, $ZrO_2$ and BeO on top of the first layer.

In an embodiment, tempering processes are carried out after the deposition of the first layer as well as after the deposition of the second layer.

In an embodiment, a gas sensor made in accordance with the present invention comprises a first gas-sensitive layer comprising gallium oxide and a second layer disposed on top of the gas-sensitive layer, the second layer comprising a material selected from the group consisting of $SiO_2$, $TiO_2$, $WO_3$, TaO, $AlVO_4$, MgO, $ZrO_2$ and BeO.

A method of manufacturing a gas sensor in accordance with the present invention includes the step of depositing a gas-sensitive first layer comprising gallium oxide on a substrate followed by depositing a second layer on top of the first layer comprising a material selected from the group consisting of $SiO_2$, $TiO_2$, $WO_3$, TaO, $AlVO_4$, MgO, $ZrO_2$ and BeO.

A filter layer comprising silicon dioxide ($SiO_2$) has the advantage that it is not sensitive to aggressive gases.

In an embodiment, the thickness of the filter layer is between about 300 and about 500 nm, since if the filter layer is too thin the selectivity disappears, and if the filter layer is too thick the sensitivity is too strongly reduced.

In order to improve the sensitivity of the gas sensor to $H_2$, the operating temperature should lie between about 600° C. and about 700° C. At a lower temperature, the electrical resistance of the gas-sensitive layer is too high. At a higher temperature, the sensitivity to $H_2$ decreases.

BRIEF DESCRIPTION OF THE PRESENTLY PREFERRED EMBODIMENTS

The invention is explained in more detail in the following drawings.

FIG. 3 is a graphical comparison of a conventional $Ga_2O_3$ sensor and a sensor of the present invention.

FIG. 4 is a graphical comparison of a conventional $Ga_2O_3$ sensor and a sensor of the present invention, but for other measurement gases than in FIG. 3.

FIG. 5 is a graphical comparison of a conventional gas sensor, operated at 600° C., with a sensor of the present invention, which is likewise operated at 600° C. and which is coated with a layer of titanium oxide.

FIG. 6 is a graphical comparison of a conventional gallium oxide sensor with a gas sensor of the present invention coated with titanium oxide, but for other measurement gases than in FIG. 5.

FIG. 7 is a graphical comparison of a conventional gallium oxide sensor at an operating temperature of 700° C. with a gas sensor of the present invention, which is likewise operated at 700° C. and is coated with tantalum oxide.

FIG. 8 is a graphical comparison of a conventional gallium oxide sensor with a sensor of the present invention coated with tantalum oxide, but for other measurement gases than in FIG. 7.

FIG. 9 is a graphical comparison of a conventional gallium oxide sensor at an operating temperature of 700° C. with a sensor of the present invention, likewise operated at 700° C., and coated with aluminum vanadate before the second tempering process.

FIG. 10 is a graphical comparison of a conventional gallium oxide sensor with a sensor of the present invention, which was coated with aluminum vanadate before the second tempering process, but for other measurement gases than in FIG. 9.

FIG. 11 is a graphical comparison of a conventional gallium oxide sensor at an operating temperature of 600° C. with a sensor of the present invention at an operating temperature of 500° C. that was coated with aluminum vanadate before the second tempering process.

FIG. 12 is a graphical comparison of a conventional gallium oxide sensor with a gas sensor of the present invention that was coated with aluminum vanadate before the second tempering process, but for other measurement gases than in FIG. 11.

FIG. 13 is a graphical comparison of the sensitivity of a gas sensor of the present invention that was coated with aluminum vanadate before the second tempering process for various measurement gases at various operating temperatures (700° C., 800° C. and 900° C.).

FIG. 14 is a graphical comparison of a conventional gallium oxide sensor, at an operating temperature of 900° C., with a gas sensor of the present invention that was coated with aluminum vanadate before the second tempering process.

FIG. 15 is a graphical comparison of a conventional gallium oxide sensor at an operating temperature of 1000° C. with a gas sensor of the present invention, likewise operated at 1000° C., that was coated with aluminum vanadate before the second tempering process.

FIG. 16 is a graphical comparison of a conventional gallium oxide sensor with a sensor of the present invention that was coated with aluminum vanadate before the second tempering process, but for other measurement gases than in FIG. 17.

FIG. 17 illustrates graphically, the sensitivity of a gas sensor of the present invention coated with tungsten oxide.

FIG. 18 illustrates graphically, the sensitivity of a conventional gallium oxide sensor at an operating temperature of 600° C., whereby the conventional sensor is exposed to the same measurement conditions as are shown in FIG. 15.

It should be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted. It should be understood, of course, that the invention is not necessarily limited to the particular embodiments illustrated herein.

DETAILED DESCRIPTION OF THE PRESENTLY PREFERRED EMBODIMENTS

Figure 1:
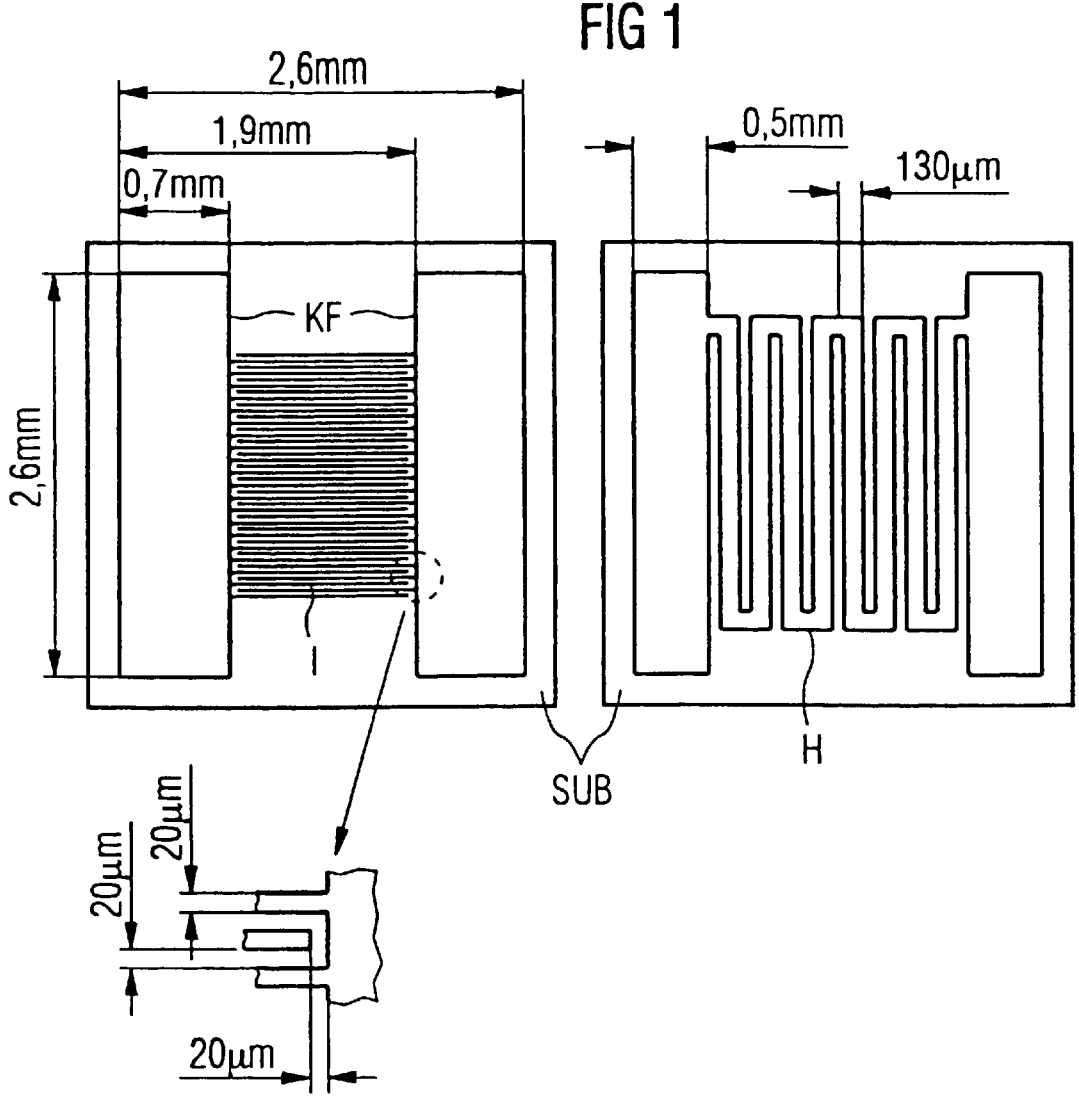
FIG. 1 is a top view and a bottom view of the sensor of the present invention.

A sensor of the present invention is shown in a top view at the left of FIG. 1. On a substrate SUB, metallic contact surfaces KF are provided, between which an interdigital structure I is arranged. A segment of the interdigital structure I is shown in an enlarged view at the bottom of FIG. 1. A gas-sensitive layer of $Ga_2O_3$ is provided above the interdigital structure I. A heating arrangement H is attached to the underside of the substrate SUB, shown at the right in FIG. 1.

Figure 2:
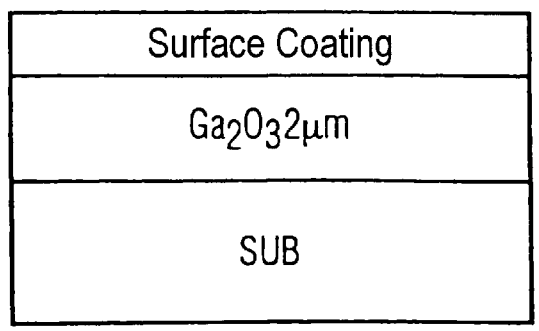
FIG. 2 is a schematic representation of a cross-section of the sensor of the present invention.

FIG. 2 shows the sensor in highly simplified form in a cross-section. A 2 $\mu$m-thick layer of $Ga_2O_3$ is deposited on the substrate SUB. A filter layer of $SiO_2$, also designated as a surface coating, is arranged above this layer. The thickness of the filter layer is about 300 nm but may range from about 300 nm to about 500 nm. For simplicity, the interdigital structure I and the heating arrangement H are not shown in FIG. 1.

In FIG. 3, a gas sensor of the present invention is compared with a conventional sensor based on $Ga_2O_3$. In the lower part of FIG. 3, how long the sensor is exposed to which gas is plotted over time t (in minutes). The reactions of the conventional gallium oxide sensor and of a sensor modified with $SiO_2$ (=sensor of the present invention) in the respectively prevailing measurement gas can be learned from the two diagrams above the lower part of the figure. The resistance R in kOhms is plotted on the ordinate of the two diagrams. The bars plotted in the lower part of the diagram under the respective measurement gases are not related to one another, but serve only to monitor whether the flow of gas was present and constant. Up to time t=350 min, a constant humidity prevails. After time t=350 min, the relative humidity (=concentration of water) is reduced from 26% to 13% for about 20 min. At time t=190 min, the concentration of oxygen is reduced from 20% to 1% for about 20 min. I.e., 98% nitrogen, 1% $H_2O$ and 1% oxygen are then present in the gas mixture to be examined. Concentrations are respectively chosen that are to be expected in a technical application.

It can be seen clearly that the sensitivity S for hydrogen ($H_2$) is considerably higher in the inventive gas sensor, namely S=53, than in the conventional gas sensor, namely S=5.5. The inadequate selectivity of the conventional gas sensor can also be detected in a comparison of the two diagrams. A clear cross-sensitivity is exhibited for oxygen ($O_2$), ammonia ($NH_3$), methane ($CH_4$) and isobutylene. The sensitivity S results from the quotient of the ohmic resistance of the sensor in synthetic air and the ohmic resistance of the sensor in the measurement gas.

The changes in the sensitivities are likewise entered in FIG. 4, but, in contrast to FIG. 3, dependent on ethanol and acetone.

The comparison of the sensor of the present invention with the conventional gas sensor shows that it was possible to reduce the sensitivity to methane, ethanol and isobutylene by means of the $SiO_2$ surface coating, whereas the sensitivity to hydrogen increased considerably. The $SiO_2$ layer is permeable only for hydrogen. This means that the air humidity is warded off by the gas-sensitive layer, whereby the resistance of the inventive sensor is higher by a factor of 5 in relation to the conventional sensor (cf. FIG. 3, ca. 1 MOhm in the conventional gas sensor and 5 MOhm in the inventive gas sensor). The sensitivity to hydrogen thus also increases in the sensor. In the test, both sensors were operated at an operating temperature of 700° C.

The inventive sensor can be realized advantageously in a planar technology that is economical and microsystem-compatible. From the point of view of the reproducibility of the manufacturing technology, the planar technology is to be preferred to the bulk-ceramic construction.

The sensors of the first embodiment of the present invention are manufactured in accordance with the following steps.

The $Ga_2O_3$ sensor is manufactured in the known way, e.g. by depositing. The crystallinity and stoichiometry of the $Ga_2O_3$ layer can be improved by means of a first tempering process at temperatures between 700 and 1200° C.

The additional layer of $SiO_2$ is deposited on the surface of the $Ga_2O_3$ with a thickness of from a few nanometers to micrometers. The modification of the surface can ensue by means of cathode sputtering, CVD, electron beam vaporization, molecular beam method or wet-chemical methods (sol-gel process).

This surface is stabilized by means of a suitable second tempering process.

By means of the surface coating, the gas sensitivity can be influenced to a high degree. The sensitivities to particular gases can be increased, and the cross-sensitivities to disturbing gases can be reduced or, in part, completely removed.

The filtering effect of the $SiO_2$ layer is based on 2 effects:

On the one hand, the size of the pores of the layer decides which gas particles reach the gas-sensitive material. On the other hand, the polar character (hydrophilic, hydrophobic) of the gas-filtering layer and of the gases is decisive. It is thus conceivable that only polar or non-polar gas molecules can pass through the filter layer, dependent on the polar state thereof (e.g. humidity blocking due to hydrophobic membrane). That is, if the gas and the filter layer have different polar states, the gas cannot penetrate the filter layer.

Not only the selectivity, but also the sensitivity for particular gases can be improved by the filtering layer made of $SiO_2$. This behavior can be explained by the fact that, in practice, the gases to be detected occur in connection with humidity. The humidity can be held back by means of the filtering layer. The sensitivity thereby increases, since it is calculated as the quotient of the electrical resistance of the sensor in synthetic air and the electrical resistance of the sensor in the gas to be detected. In addition, the sensitivity to $NH_3$ decreases, which in a conventional gas sensor has a strong measurement effect in dry air. Since the layer that is not transparent to humidity prevents the coating of the $Ga_2O_3$ surface with OH groups, a sensor with a high measurement sensitivity to $NH_3$ can be manufactured.

The material that is to be used as the filtering layer has to have an electrical conductivity that is less than that of the gas-sensitive layer by at least a factor of 10. In addition, the material may not react with the gas-sensitive layer, and may not effect any catalytic conversion of the gases. Non-porous, amorphous $SiO_2$ is a material with the above-named characteristics.

In materials with filtering characteristics, e.g. fullerene, whose electrical conductivity is too high, or materials that react with the gas-sensitive layer, such as for example by means of interdiffusion or solid-state chemical reactions, a non-conducting $SiO_2$ layer up to about 30 nm thick can be brought between the gas-sensitive layer and the filter layer.

The operating temperature of the gas sensor has to lie between 600° C. and 700° C. At a lower temperature, the electrical resistance of the gas-sensitive $Ga_2O_3$ layer is too high. At a higher temperature, the sensitivity to $H_2$ is lost.

The substrate SUB, on whose one side the heating arrangement H is deposited, and on whose other side the measurement electrodes are deposited in the form of an interdigital structure I in connection with the gas-sensitive $Ga_2O_3$ layer and the filter layer, can consist of an $Al_2O_3$ (aluminum oxide) layer and an electrically non-conductive $SiO_2$ (silicon dioxide) layer lying above it. The $SiO_2$ layer simultaneously represents a diffusion blocking layer.

In a second embodiment, a 2 $\mu$m-thick $Ga_2O_3$ layer is deposited on the substrate SUB (cf. FIG. 2). A gas-sensitive metal oxide layer is deposited over this layer. The thickness of the gas-sensitive metal oxide layer (also called the second layer) depends on the metal oxide used. As a rule, it lies between 30 nm and 300 nm.

The gas sensor of the second embodiment of the present invention is manufactured as follows.

On the substrate SUB, which is coated on one side with the heating electrode structure H and on the other side with the measurement electrode structure I, a 2 $\mu$m-thick gallium oxide layer is deposited. The depositing takes place e.g. by means of sputtering. There subsequently ensues a first tempering process at a tempering temperature $\theta_T$ between 700 and 1200° C. By this means, the crystallinity and the stoichiometry of the gallium oxide layer is improved. In a next step, a gas-sensitive metal oxide layer with a layer thickness of 3 to 300 nm is deposited on the surface of the gallium oxide. This surface modification can be produced by cathode sputtering CVD, electron beam vaporization, molecular beam method or a wet-chemical method.

For the second layer, gas-sensitive metal oxides, such as titanium oxide ($TiO_2$), aluminum vanadate ($AlVO_4$), $V_2O_5$, tungsten oxide ($WO_3$) or tantalum oxide (TaO) can be used. There subsequently ensues a second tempering process that lasts about 15 hours and whose temperature $\theta_T$ lies between 850° C. and 1100° C., depending on the operating temperature $\theta_B$. In principle, the tempering temperature $\theta_T$ is to be chosen higher than the intended operating temperature $\theta_B$. In the following table, the corresponding layer thickness, the tempering temperature $\theta_T$, the operating temperature $\theta_B$ and the respective gas sensitivity of the sensor are indicated for the respective gas-sensitive metal oxide.

| Metal oxide | Thickness [nm] | $\theta_T$ [° C.] | $\theta_B$ [° C.] | Sensitivity |
|---|---|---|---|---|
| $TiO_2$ | 300 | 650 | 600 | Solvent |
| $AlVO_4$ | 300 | 750 | 700 | $O_2$ sensor |
| $AlVO_4$ | 300 | 950 | 700–900 | not sensitive = reference element |
| $AlVO_4$ | 300 | 750 | 500 | $NH_3$ (ammonia) |
| $AlVO_4$ | 30 | 1050 | 1000 | not sensitive to ethanol ($C_2H_5OH$), but sensitive to methane ($CH_4$) |
| $WO_3$ | 30 | 350 | 300 | NO sensor |
| TaO | 300 | 750 | 700 | ethanol sensor |

A second layer of aluminum vanadate, deposited after the first tempering process, becomes vanadium pentoxide ($V_2O_5$) by means of the second tempering process.

The electrons contributed for the modification of the conductivity come from the gas-sensitive metal oxide layer (2nd layer), but not from the gallium oxide. The electrons or, respectively, the electrical field migrate from the gas-sensitive metal oxide into the gallium oxide, and cause a change of conductivity there. The gas-sensitive characteristics of the gallium oxide are not exploited, but rather those of the metal oxide deposited as a second layer, or, respectively, of a combination of the second layer and gallium oxide.

In a conventional gallium oxide sensor, the gas to be measured is chemically absorbed on the surface of the gallium oxide layer, or surface reactions occur on the semiconducting gallium oxide layer, and there results an electron transfer of the adsorbate and sensor material, and thereby an increase in conductivity.

If the surface of the gallium oxide layer is changed by the depositing of some atom layers of another gas-sensitive metal oxide, two positive effects result.

First, electrons generated by the surface through the gas effect flow into the $Ga_2O_3$ layer. At low temperatures (600° C.), only very few electrons ($10^{-13}/cm^3$) are present there, whereby a large Debye length is present. As a consequence, electrons that flow into the gallium oxide layer have a large effect on the conductivity (a factor of about 10).

Second, the chemical absorption of particular gases, e.g. NO or $NH_3$, is promoted or, respectively, inhibited by the specially selected gas-sensitive metal oxide (2nd layer). By this means, the sensitivity (=selectivity) can be purposively increased for particular gases. In FIGS. 5 to 16, sensors with modified surfaces and an uncoated $Ga_2O_3$ sensor (=conventional sensor) are respectively compared. The representation of the cited measurement diagrams corresponds to the representation of the measurement diagrams shown in FIGS. 3 and 4.

In FIGS. 17 and 9, the resistance of the sensor in the test gas is briefly higher than the resistance of the sensor in synthetic air. In order to enable a better comparison of the sensitivities at this point, the reciprocal value of the sensitivity S is indicated there.

The following examples are provided for selective sensors that comprise a gas-sensitive metal oxide layer.

a) Solvent sensor: FIG. 5 illustrates the gas-sensitive behavior of a gas sensor provided with a titanium oxide layer (layer thickness 300 nm) in comparison with a conventional (uncoated) $Ga_2O_3$ sensor. The second tempering process was carried out periodically at a tempering temperature $\theta_T=650°$ C. The operating temperature is $\theta_B=600°$ C. The inventive sensor is suited for solvents. The sensitivity for ethanol is 17, for acetone is 12, and for isobutylene is 4.2. For all other measured gases, the sensitivity is less than 1.5. The electrical resistance of the sensor in synthetic air is lower by about a factor of 10 than for the conventional gallium oxide sensor. The reaction time of the inventive gas sensor can be reduced in relation to the conventional gallium oxide sensor.

b) Ethanol sensor: FIGS. 7 and 8 illustrate the gas-sensitive behavior of a gas sensor coated with tantalum oxide (layer thickness 300 nm) in comparison with an untreated $Ga_2O_3$ sensor. The second tempering process was carried out at $\theta_T=750°$ C. The operating temperature is $\theta_B=700°$ C. Both sensors react predominantly to ethanol, with a sensitivity of S=19. For all other measurement gases, the sensitivity of the inventive sensor is less than 1.7. The electrical resistance of the inventive sensor in synthetic air is lower by a factor of 5 than that of the conventional gas sensor.

c) Oxygen sensor: FIGS. 9 and 10 illustrate the gas-sensitive behavior of a gas sensor coated with aluminum vanadate (layer thickness 300 nm) in comparison to an uncoated $Ga_2O_3$ sensor. The second tempering process was carried out at $\theta_T=750°$ C. The operating temperature is $\theta_B=700°$ C. The inventive sensor reacts to oxygen ($O_2$) with a reciprocal sensitivity of 1/S=2.1 and to ammonia with a sensitivity S=1.1. The sensitivity of the inventive gas sensor to the other indicated measurement gases is imperceptibly low. The electrical resistance of the inventive sensor to synthetic air is smaller by about a factor of 100 than that of the conventional gas sensor. Moreover, the sensor signal of the inventive gas sensor is very stable, and its reaction time is small.

d) Ammonia sensor: FIGS. 11 and 12 illustrate the gas-sensitive behavior of a gas sensor coated with aluminum vanadate (layer thickness 300 nm) in comparison with a conventional $Ga_2O_3$ sensor. The tempering temperature $\theta_T=750°$ C. and the operating temperature (deviating from the oxygen sensor indicated under point c)) is $\theta_B=500°$ C. The inventive sensor shows a sensitivity of S=2.1 to ammonia ($NH_3$) and a very low sensitivity to hydrogen ($H_2$). The electrical resistance of the inventive sensor in synthetic air is here also substantially lower than in a conventional $Ga_2O_3$ sensor. The sensor signal of the inventive sensor is very stable.

e) Reference sensor: FIGS. 13 and 14 illustrate the gas-sensitive behavior of a gas sensor provided with an aluminum vanadate layer (layer thickness 300 nm) in comparison with a conventional $Ga_2O_3$ sensor. The tempering temperature is $\theta_T=950°$ C. At an operating temperature $\theta_B$ between 700° C. and 900° C., the inventive sensor reacts to a change in the oxygen content only with a sensitivity S=1.2. The sensitivities to other measurement gases is considerably lower. The indicated inventive sensor can be used as a gas-insensitive reference element.

f) Methane sensor: FIGS. 15 and 16 illustrate the gas-sensitive behavior of a gas sensor coated with aluminum vanadate (layer thickness 30 nm) in comparison with a conventional $Ga_2O_3$ sensor. The tempering temperature $\theta_T$ is 1050° C. and the operating temperature $\theta_B$ is 1000° C. The advantage of this inventive sensor lies not in its selectivity for methane, but rather in the reduction of its sensitivity to ethanol, which can have a particularly disturbing effect for certain applications. The sensitivity to ethanol was reduced by a factor of 2, and that of methane was reduced to the factor 4, if equal reaction times are assumed. The methane sensitivity was hereby more strongly reduced. Even at very much higher concentrations of ethanol, which is not very stable, a higher sensitivity is hardly caused, whereas in contrast for methane the concentration is already present that is also supposed to be detected in the technical application of the sensor. In a conventional gallium oxide sensor, at higher concentrations the ethanol sensitivity increases by an order of magnitude.

g) Nitrogen monoxide sensor: FIGS. 15 and 16 illustrate the gas-sensitive behavior of a gas sensor coated with tungsten oxide (layer thickness 30 nm) in comparison with an untreated $Ga_2O_3$ sensor. The tempering temperature $\theta_T$ is 350° C. and the operating temperature $\theta_B$ is 300° C. Due to the high electrical resistance of the sensitive layer, a conventional gallium oxide sensor cannot be operated below 600° C. Since the highest NO sensitivity is present at 600° C., this operating temperature is used for the comparison. The extremely high sensitivity of the inventive gas sensor to NO, greater by a factor of about 100 (1/S compared with S), can be seen. The electrical resistance of the inventive sensor in air is about 1 megohm, and is thus likewise smaller by a factor of 100 than that of the conventional gallium oxide gas sensor.

Sensors of the present invention are advantageously manufactured in economical and microsystem-compatible planar technology. From the point of view of the reproducibility of the manufacturing technology, this technology is to be preferred to bulk-ceramic constructions.

By means of the depositing of a gas-sensitive metal oxide layer, the gas sensitivity can be influenced to a high degree.

The sensitivities to particular target gases can be increased, and the cross-sensitivities to interfering gases can be reduced or, in part, completely removed. It was possible to strongly reduce the very high sensitivity to ethanol of a conventional gallium oxide gas sensor, whereby the methane sensitivity decreased only slightly (cf. FIG. 16).

The gas-insensitive reference element according to FIGS. 13 and 14 can be used for the elimination of temperature fluctuations. By this means, a regulation of the temperature of the sensor is no longer necessary. On this subject, we refer to the application P 44 32 729.3. A gas sensor is indicated there that comprises a gas- and temperature-dependent arrangement and, arranged in the immediate vicinity thereof, an arrangement that is temperature-dependent only. By means of the formation of differences or ratios of the output signals of the two arrangements, a measurement variable can be obtained that is independent of temperature fluctuations and remains only gas-dependent. The first layer of $Ga_2O_3$ provides the stable electrical basic conductivity.

From the above description, it is apparent that the objects and advantages of the present invention have been achieved.

While only certain embodiments have been set forth, alternative embodiments and various modifications will be apparent from the above description to those skilled in the art. These and other alternatives are considered equivalents and within the spirit and scope of the present invention.

We claim:

1. A gas sensor comprising:

a gas-sensitive layer comprising $Ga_2O_3$, and a filter layer disposed on top of the gas-sensitive layer, the filter layer comprising $SiO_2$ and having a thickness from 300 nm to 500 nm, the filter layer being impermeable except for $H_2$, the sensor having an operating temperature ranging from 600° C. to 700° C.

2. The gas sensor of claim 1 wherein the gas sensitive layer has a thickness of about 2 µm.

* * * * *